United States Patent [19]
Liu et al.

[11] Patent Number: 5,001,265
[45] Date of Patent: Mar. 19, 1991

[54] AQUEOUS REDUCTION PROCESS FOR HALO-NITRO-PHENOLS

[75] Inventors: Ming-Biann Liu, Clayton, Calif.; Luke R. Kleiss, Lisle, Ill.

[73] Assignee: The Dow Chemical Company, Midland, Mich.

[21] Appl. No.: 386,056

[22] Filed: Jul. 28, 1989

[51] Int. Cl.$^5$ .................. C07C 209/36; C07C 209/74
[52] U.S. Cl. ..................................... 564/418; 564/417; 564/420
[58] Field of Search ........................ 564/417, 418, 420

[56] References Cited

U.S. PATENT DOCUMENTS

| | | | |
|---|---|---|---|
| 3,079,435 | 2/1963 | Freifelder et al. | 564/418 X |
| 3,666,813 | 5/1972 | Hindin et al. | 564/417 |
| 4,020,107 | 4/1977 | Kosak | 564/417 |
| 4,329,503 | 5/1982 | Bauer et al. | 564/418 |
| 4,766,244 | 8/1988 | Lysenko | 564/418 |
| 4,885,389 | 12/1989 | Lee et al. | 564/418 |

OTHER PUBLICATIONS

G. M. Loudon, *Organic Chemistry* 1197–98 (Addison–Wesley Publ. Co. 1984); R. T. Morison et al. *Organic Chemistry*–3rd ed., 737–38 (Allyn & Bacon 1973).

*Primary Examiner*—Richard L. Raymond

[57] ABSTRACT

An aminophenolic compound can be synthesized by contacting a halo-nitro-phenolic compound, such as 2-chloro-4,6-dinitrorescorcinol, with a hydrogenating agent, such as hydrogen, and a catalyst, such a palladium-on-carbon, in an aqueous solution in the presence of an acid such as phosphoric acid.

26 Claims, No Drawings

AQUEOUS REDUCTION PROCESS FOR HALO-NITRO-PHENOLS

BACKGROUND OF THE INVENTION

This invention relates to the art of synthesizing aminophenols.

Metal catalyzed hydrogenation of halo-dinitro-dihydroxy benzenes is known to be useful for synthesizing diaminobenzenediols, such as 4,6-diaminoresorcinol, which are useful as monomers for polybenzoxazole polymers. See Lysenko, *High Purity Process for the Preparation of 4,6-Diamino-1,3-benzenediol,* U.S. Pat. No. 4,766,244 (Aug. 23, 1988) which is incorporated herein by reference. During hydrogenation, the halogen is removed from the aromatic ring as hydrogen halide.

Halogen is difficult to remove by hydrogenation from the aromatic ring of aminophenol compounds when the aminophenol moiety is protonated. Hydrogenation of halo-nitro-phenolic compounds is ordinarily carried out under basic conditions, so that the amine group produced by hydrogenation of the nitro group is not protonated. However, the free base of the aminophenolic product is unstable with respect to oxidation in aqueous media, so the hydrogenation is ordinarily carried out in organic solvents. See U.S. Pat. No. 4,766,244 at column 3, lines 52–59. Organic solvents are very costly to use in commercial scale production. Furthermore, organic solvents can present an undesirable fire risk, particularly in the presence of flammable hydrogenation catalysts and potentially explosive nitrated phenols. What is needed is a high yield process for the synthesis of aminophenolic compounds which can be practiced in an aqueous medium containing either reduced levels of organic solvent or no organic solvent at all.

SUMMARY OF THE INVENTION

The present invention is a process for synthesizing an aminophenolic compound, said process comprising the step of contacting a halo-nitro-phenolic compound with a hydrogenating agent in the presence of a noble metal hydrogenation catalyst in an aqueous solvent containing less than 50 percent by weight organic diluent and in the presence of an acid which is a weaker acid than the hydrogen halide of the halogen atom in the halo-nitro-phenol, is stable under reaction conditions, and does not interfere with the functioning of the catalyst, under conditions such that an aminophenolic compound is formed.

The process of the present invention offers the advantage of minimizing or eliminating organic solvents in the hydrogenation, thereby reducing manufacturing cost and the risk of fire in the system. The process can be used to synthesize aromatic compounds having at least one primary amine moiety and at least one hydroxy moiety bonded to the aromatic ring (aminophenolic compounds). Aminophenolic compounds are useful as intermediates in the synthesis of dyes and pharmaceuticals, and as photographic developers, as described in 2 Encyclopedia Chem. Tech.-3rd Ed., *Aminophenols.* 422–40 (J. Wiley & Sons 1978). Aminophenolic compounds having a single primary amine moiety ortho to a single hydroxy moiety are useful as chain-terminating agents for polybenzazole polymers, as described in U.S. Pat. No. 4,703,103, which is incorporated herein by reference. Aminophenolic compounds having two primary amine groups and two hydroxy groups, one ortho to each amine group, are useful as co-monomers for synthesizing polybenzoxazole (PBO) polymers, as described in 11 Ency. Poly. Sci. & Tech., *Polybenzothiazoles and Polybenzoxazoles* 601 (1988), which is incorporated herein by reference.

DETAILED DESCRIPTION OF THE INVENTION

The process of the present invention utilizes the catalytic hydrogenation of a halo-nitro-phenol. The halo-nitro-phenol comprises an aromatic ring bonded to a halogen atom, a hydroxy group and a nitro group. It more preferably further comprises a second hydroxy group and a second nitro group bonded to the aromatic ring. Each nitro group is preferably ortho to a hydroxy group. When the halo-nitro-phenol contains two hydroxy groups and two nitro groups, each nitro group is preferably ortho to a different hydroxy group.

The hydroxy group is preferably ortho to the halogen atom. When the halo-nitro-phenol contains two hydroxy groups and two nitro groups, both hydroxy groups are preferably ortho to the halogen atom. The halogen bonded to the aromatic ring is preferably chlorine, bromine or iodine and more preferably chlorine.

The aromatic ring may be heterocyclic, such as pyridine, but is preferably carbocyclic. The aromatic ring may have substituents other than the hydroxy, nitro and halogen substituents previously described, which are stable under reaction conditions and do not interfere with the reaction. Examples of other substituents include a second halogen atom, a second hydroxy moiety, an amine moiety, a phenyl moiety, a phenoxy moiety, an alkoxy moiety and a lower (about 1–6 carbon) alkyl moiety. The aromatic ring most preferably has no substituents other than those specifically identified.

Examples of suitable halo-nitro-phenols include 2-halo-6-nitro-phenol and 2-halo-4,6-dinitroresorcinol. The halo-nitro-phenol is most preferably a 2-halo-4,6-dinitroresorcinol.

Halo-nitro-phenolic compounds having only a single nitro and hydroxyl group preferably conform to formula 1(a):

                                1(a)

and more preferably conform to formula 1(b):

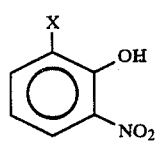
                                  1(b)

wherein Ar comprises an aromatic ring and X is a halogen as previously described.

Halo-nitro-phenolic compounds having two nitro groups and two hydroxyl groups preferably comply with formula 2(a):

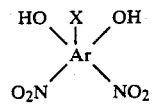
                                  2(a)

and more preferably comply with either formula 2(b) or 2 (c):

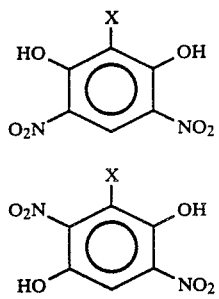

wherein Ar and X have the meaning and preferred embodiments previously given. The halo-nitro-phenolic compound most preferably complies with formula 2(b). Examples of suitable halo-nitro-phenols include 4,6--dinitro-2-chlororesorcinol; 4,6-dinitro-2-bromoresorcinol: 2,5-dinitro-3-chlorohydroquinone; and 2-chloro-5-nitrophenol.

Halo-nitro-phenolic compounds can be synthesized by obvious substitution of reagents into known processes. For instance, they may be synthesized by nitrating an appropriate aromatic di- or trihalide, followed by displacement of one or more halogen atoms with hydroxy groups as described in U.S. Pat. No. 4,766,244, which is incorporated herein by reference. Alternatively, halo-nitro-phenolic compounds may be synthesized by halogenation and nitration of phenolic compounds under conditions described in Loudon, *Organic Chemistry* 757–61 (Addison-Wesley Publ. Co. 1984).

The halo-nitro-phenol is contacted with a hydrogenating agent. The hydrogenating agent may be any known hydrogenating agent which can be used in an aqueous solution, but it is preferably molecular hydrogen. The hydrogenating agent should be present in at least a stoichiometric amount, and is preferably present in a stoichiometric excess over the amount of halo-nitro-phenolic compound.

The contact is made in an aqueous solution. Due to the insolubility of many halo-nitro-phenolic compounds, the halo-nitro-phenolic compound frequently forms a slurry in water. The amount of water should be sufficient to dissolve enough hydrogen for a reasonable rate of reaction and to leave the slurry reasonably stirrable. The maximum amount of water is governed primarily by practical considerations. At higher ratios of water to halo-nitro-phenolic compound, the capacity of the reaction equipment is necessarily lower. The ratio of halo-nitro-phenolic compound to water is preferably at most about 0.8 mole per liter, more preferably at most about 0.7 mole per liter and most preferably at most about 0.68 mole per liter.

The water may be mixed with organic diluents, such as alkanols and glycols, which are miscible with water. The term "organic diluent" does not refer to the acid or the halo-nitro-phenolic compound, but only to organic compounds which function as solvents. The organic diluent preferably makes up a small enough part of the solution to minimize the flame hazard resulting from its presence. The organic diluent should make up no more than 50 percent of the solvent by weight, preferably no more than 25 percent and more preferably no more than 10 percent. The solvent most preferably contains essentially no organic diluent, such that water is the only solvent.

The reaction takes place in the presence of a noble metal hydrogenation catalyst. Suitable noble metals are those known to promote both hydrogenation of nitro groups and hydrogenation of aromatic halides to form aromatic rings and hydrogen halide. Examples of suitable noble metals include gold, silver, platinum, palladium, iridium, rhodium, mercury, ruthenium and osmium. Preferred metals are platinum and palladium and the most preferred metal is palladium. The catalyst metal may be used in any form which is suitable to catalyze the reaction. For instance, some catalyst metals may be used as a metal oxide, although the catalyst metal is preferably in an unoxidized state. The catalyst may be used in bulk, but is preferably supported by a support, such as carbon. The most preferred catalyst is palladium-on-carbon. Palladium-on-carbon catalysts preferably contain at least about 5 weight percent palladium and more preferably at least about 10 weight percent palladium.

The amount of catalyst used is governed essentially by practical considerations which are familiar to persons of ordinary skill in the art. The reaction takes very long at very low catalyst levels, and the cost of catalyst is uneconomical at high catalyst levels. When the catalyst is 10 percent palladium-on-carbon, the weight percentage of catalyst to halo-nitro-phenolic compound is preferably at least about 1 percent, more preferably at least about 3 percent and most preferably at least about 6 percent. The weight ratio is preferably at most about 15 percent and more preferably at most about 8 percent.

The reaction takes place in the presence of an acid which is a weaker acid than the hydrogen halide of the halogen in the halo-nitro-phenolic compound. For instance, the $pK_a$ of the acid should be no less than $-6.1$ when the halogen of the halo-nitro-phenolic compound is chlorine, because that is the $pK_a$ of hydrogen chloride. The $pK_a$ should be sufficiently low for the acid to stabilize an o-aminohydroxy moiety on the resulting compound. The $pK_a$ of the acid is preferably greater than $-3$, more preferably at least about 0 and most preferably at least about 1. The $pK_a$ is preferably less than 10, more preferably at most about 4.75 and most preferably at most about 2.75.

The acid must be stable under reaction conditions. For instance, trichloroacetic acid tends to form hydrogen halide under reaction conditions, and is unsuitable for the present process, although trifluoroacetic acid is stable and is suitable.

The acid must also not interfere with the action of the catalyst. Phosphonic acid, hypophosphoric acid, sulfuric acid, sulfonic acid, benzenesulfonic acid and toluenesulfonic acid all interfere with catalyst activity and are inappropriate for the present invention. It is theorized, without intending to be bound, that acids which contain aromatic structures or incomplete octet structures can become adsorbed upon and/or associated with the catalyst metal, thereby obstructing reagents from access to the catalyst.

Examples of suitable acids include phosphoric acid, boric acid, trifluoroacetic acid, fluoboric acid, methanesulfonic acid, propionic acid, heptanoic acid and acetic acid. Preferred acids are phosphoric acid, methanesulfonic acid, fluoboric acid and trifluoroacetic acid. Trifluoroacetic acid and phosphoric acid are more preferred, and phosphoric acid is most preferred.

The acid should be used in at least a stoichiometric ratio with nitro groups in the halo-nitro-phenolic moiety. However, excess acid reduces the solubility of hydrogen in water, thereby lengthening the time needed for the reaction. When the halo-nitro-phenol is 2-chloro-4,6-dinitroresorcinol and the acid is phosphoric acid, the molar ratio of acid to halo-nitro-phenol is preferably at least about 1:1 and more preferably at least about 2:1. The molar ratio of acid to halo-nitro-phenol is preferably at most about 10:1, more preferably at most about 5:1 and most preferably at most about 4:1. The pH of the slurry varies widely depending upon the acid used, but is preferably between about 1 and 2 for phosphoric acid.

The hydrogenating agent may be introduced into the slurry by any means effective to achieve a reasonable dispersion. For instance, hydrogen may be sparged into the slurry or introduced into the headspace and dispersed with an entrainment agitator. Good agitation is important to maintain an even dispersion of reagents throughout the system. The temperature of the reaction may be any at which the reaction proceeds and the reagents and products are stable. The maximum temperature achieved during the reaction is preferably at least about 15° C., more preferably at least about 45° C. and most preferably at least about 50° C. It is preferably at most about 100° C., more preferably at most about 65° C. and most preferably at most about 55° C. The reaction should be carried out under a non-oxidizing atmosphere.

Catalyst is preferably removed from the reaction mixture by known means such as filtration.

The aminophenolic product contains an aromatic ring, one or more hydroxyl groups bonded to the aromatic ring in the same positions as the hydroxy groups on the halo-nitro-phenol, one or more primary amine groups bonded to the aromatic ring in the positions formerly occupied by the nitro groups on the halo-nitro-phenol, a hydrogen in each position formerly occupied by a halogen atom. The product is more susceptible to air oxidation while in solution or wet, so it is preferably precipitated and dried as soon as possible. The product in solution is protonated, and is more stable with respect to air oxidation if it is precipitated as an acid salt. Precipitation can be accomplished by any combination of known methods, such as cooling the solution, adding a non-solvent or raising the pH of the solution to decrease solubility. Examples of suitable non-solvents include alkanols such as methanol, ethanol and propanol. Examples of suitable neutralizing agents include alkali metal bicarbonate, ammonium bicarbonate, sodium hydroxide and tertiary amines.

It is theorized that hydrogen halide generated in the reaction tends to displace the weaker acids used in protonating amine groups on the product. If the salt is precipitated without neutralizing acid to raise the pH of the solution, then the precipitated product will be at least in part a hydrogen halide salt. It can be precipitated as a completely hydrogen halide salt by adding at least a stoichiometric amount of hydrogen halide acid before precipitation.

On the other hand, it is further theorized that hydrogen halide, as the stronger acid, is neutralized first if a base is added. If non-halide salt such as a phosphate salt is desired, then at least a stoichiometric amount of neutralizing agent may be added either prior to polymerization or as part of polymerization. The counterion in the resulting salt is the acid used during reduction.

The selectivity of product recovered is preferably greater than 90 percent, more preferably at least about 95 percent, and most preferably at least 98 percent based upon the starting halo-nitro-phenol.

Compounds produced by the present invention can be used as described in the references previously cited and incorporated by reference.

ILLUSTRATIVE EMBODIMENTS

The following examples are for illustrative purposes only and should not be taken as limiting either the specification or the claims. Unless stated otherwise, all parts and percentages are given by weight.

EXAMPLE 1

Hydrogenation of 2-Chloro-4,6-Dinitroresorcinol Using Trifluoroacetic Acid

A mixture containing 5.0 g (21 mmoles) of 2-chloro-4,6-dinitroresorcinol, 60.7 g of water, 0.50 g of 10 weight percent palladium-on-carbon catalyst, and 4.9 g (43 mmoles) of trifluoroacetic acid is agitated in a 500-ml, 3-necked, round-bottom flask with a magnetic stirrer. The headspace is flushed with hydrogen, and hydrogen pressure of about 1 atm is maintained throughout the reaction. The temperature is raised to 50° C. for 110 minutes. LC analysis of the resulting solution indicates that 4,6-diaminoresorcinol is synthesized with 95 percent selectivity.

EXAMPLE 2

Hydrogenation of 2-Chloro-4,6-Dinitroresorcinol With Phosphoric Acid

The procedure of Example 1 is repeated, except that trifluoroacetic acid is replaced with 4.9 g of 85 percent phosphoric acid (equal to about 43 mmoles of $H_3PO_4$). LC analysis shows a selectivity of 97 percent to 4,6-diaminoresorcinol.

EXAMPLE 3

Hydrogenation of 2-Chloro-4,6-Dinitroresorcinol

The procedure of Example 1 is repeated using about 43 mmoles of fluoboric acid. The major product recovered is 4,6-diaminoresorcinol.

EXAMPLE 4

Hydrogenation of 2-Chloro-4,6-Dinitroresorcinol Using Methanesulfonic Acid

The procedure of Example 1 is repeated using about 43 mmoles of methanesulfonic acid in place of trifluoroacetic acid. The major product recovered is 4,6-diaminoresorcinol.

EXAMPLE 5

Hydrogenation of 2-Chloro-4,6-Dinitroresorcinol Using Acetic Acid

The procedure of Example 1 is repeated using about 43 mmoles of glacial acetic acid in place of trifluoroacetic acid. LC analysis of the product shows that 4,6-diaminoresorcinol is made in 91 percent selectivity.

EXAMPLE 6

Large Scale hydrogenation of 2-Chloro-4,6-Dinitroresorcinol Using Phosphoric Acid A mixture of 261 g (1.11 moles) of 2-chloro-4,6-dinitroresorcinol, 26 g of 10 percent palladium-on-carbon catalyst, 1589 g of water and 253.5 g of 85 percent phosphoric acid is agitated with a 3-inch 8-bladed mechanical turbine agitator in a 4-liter jacketed glass reactor. The temperature of the reactor is maintained at 50° C. Air in the reactor is purged with nitrogen and 1 atm of hydrogen is introduced. At 600 rpm, stirring, the reaction is completed in 430 minutes. LC analysis of the product shows the selectivity to 4,6-diaminoresorcinol is about 97 percent.

EXAMPLE 7

Hydrogenation of 2-Chloro-4,6-Dinitroresorcinol under differing conditions, and precipitation of differing salts A 1235-g quantity of deionized water is added to a reactor under nitrogen atmosphere. A 10.7-g aqueous solution containing 0.002 g/ml sodium lauryl sulfate is added to control foaming. A 580-g quantity of wet 2-chloro-4,6-dinitroresorcinol, prepared as described in Example 1 (A) and (B) of U.S. Pat. No. 4,766,244 and having a purity of 98.46 percent by LC analysis, is added. The mixture is stirred by a mechanical impeller for 10 minutes at 220 rpm. Phosphoric acid is added in a molar ratio of 2.2 moles of phosphoric acid per mole of 2-chloro-4,6-dinitroresorcinol. A 10 percent palladium-on-carbon catalyst is added in the quantities shown in Table 1, as a weight percentage of the 2-chloro-4,6-dinitroresorcinol. The reactor is purged with hydrogen gas, and the impeller speed is raised to 750 rpm. The temperature of the mixture is then raised to the temperature in Table 1, as the reaction proceeds for the time shown in Table 1.

TABLE 1

| Sample No. | Catalyst wt. % | Temp. °C. | Time min. |
|---|---|---|---|
| 1 | 6 | 55 | 270 |
| 2 | 8 | 65 | 355 |
| 3 | 4 | 45 | 625 |
| 4 | 4 | 65 | 415 |
| 5 | 8 | 45 | 330 |
| 6 | 6 | 55 | 245 |

The catalyst is filtered, and the filtrate is added to a work-up vessel under nitrogen atmosphere with agitation of 500 rpm. Salts of the product are precipitated by one of the procedures described hereinafter.

(A) The work-up vessel is heated to 60° C. A 1025-g quantity of 37 percent hydrochloric acid containing 13 g of tin (II) chloride is added at a rate of 40 ml/min, such that the hydrogen chloride concentration of the resulting mixture is about 15 percent. The agitation is adjusted to 300 rpm, and the mixture is cooled to 10° C. The di(hydrochloride) salt of 4,6-diaminoresorcinol is filtered, washed in 15 percent HCl and dried under nitrogen atmosphere.

(B) A solution of saturated sodium bicarbonate is added gradually to a quantity of the aqueous solution at 25° C. with vigorous agitation, until the pH of the solution is 3.85. The monophosphate salt of 4,6-diaminoresorcinol is filtered, washed with 900 ml of water containing 5 g of tin (II) chloride dihydrate and 5 g of 37 weight percent hydrochloric acid, and dried at 45° C. in a vacuum oven.

(C) A solution of saturated ammonium bicarbonate is added gradually to a quantity of the aqueous solution at 25° C. with vigorous agitation, until the pH of the solution is 4.49. The monophosphate salt of 4,6-diaminoresorcinol is filtered, washed with 1000 ml of water containing 5 g of tin (II) chloride dihydrate and 5 g of 37 weight percent hydrochloric acid, and dried at 45° C. in a vacuum oven.

The organic component of each salt contains at least 98 percent to 99 percent 4,6-diaminoresorcinol.

What is claimed is:

1. A process for synthesizing an aminophenolic compound, said process comprising the step of contacting a halo-nitro-phenolic compound with a hydrogenating agent in an aqueous solvent containing no more than 50 percent organic diluent in the presence of a noble metal hydrogenation catalyst and in the presence of an acid which is a weaker acid than the hydrogen halide of the halogen in the halo-nitro-phenolic compound and is stable under reaction conditions and does not interfere with the functioning of the catalyst, under conditions such that the corresponding aminophenolic compound is formed.

2. The process of claim 1 wherein the catalyst comprises platinum or palladium.

3. The process of claim 2 wherein the catalyst comprises palladium on a support.

4. The process of claim 2 wherein the hydrogenating agent is hydrogen gas.

5. The process of claim 4 wherein the aqueous solvent contains no more than about 25 percent organic diluent.

6. The process of claim 4 wherein the aqueous solvent contains no more than about 10 percent organic diluent.

7. The process of claim 4 wherein the aqueous solvent contains essentially no organic diluent.

8. The process of claim 4 wherein the acid has a $pK_a$ between $-6.1$ and about 4.75.

9. The process of claim 4 wherein the acid has a $pK_a$ between about 0 and about 2.75.

10. The process of claim 4 wherein the acid is phosphoric acid, boric acid, trifluoroacetic acid, fluoboric acid, methanesulfonic acid or acetic acid.

11. The process of claim 4 wherein the acid is phosphoric acid, methanesulfonic acid, fluoboric acid or trifluoroacetic acid.

12. The process of claim 11 wherein the acid is trifluoroacetic acid.

13. The process of claim 11 wherein the acid is phosphoric acid.

14. The process of claim 11 wherein the halo-nitro-phenolic compound comprises an aromatic ring, a halogen atom bonded to said aromatic ring, two hydroxyl groups bonded to said aromatic ring, and two nitro groups, each bonded to said aromatic ring ortho to a hydroxy group.

15. The process of claim 11 wherein each nitro group in the halo-nitro-phenolic compound is ortho to a hydroxy group, and each hydroxy group is ortho to a halogen atom.

16. The process of claim 1 wherein the halo-nitro-phenolic compound is a 2-halo-4,6-dinitroresorcinol, wherein the halogen is chlorine or bromine.

17. The process of claim 16 wherein the halogen of the halo-nitro-phenolic compound is chlorine.

18. The process of claim 16 wherein the catalyst comprises metallic palladium.

19. The process of claim 18 wherein the hydrogenating agent is hydrogen gas.

20. The process of claim 19 wherein the acid is phosphoric acid, fluoboric acid, methanesulfonic acid or trifluoroacetic acid.

21. The process of claim 20 wherein the acid is phosphoric acid.

22. The process of claim 21 wherein the aqueous solvent contains no more than 25 weight percent organic diluent.

23. The process of claim 21 wherein the aqueous solvent contains no more than about 10 weight percent organic diluent.

24. The process of claim 21 wherein the solvent comprises essentially no organic diluent.

25. The process of claim 24 wherein the maximum temperature of the reaction is between 45° C. and 65° C.

26. The process of claim 25 wherein the process forms 4,6-diaminoresorcinol and/or a salt thereof with a selectivity of at least about 95 percent.

* * * * *